(12) United States Patent
Dong et al.

(10) Patent No.: US 6,992,768 B2
(45) Date of Patent: Jan. 31, 2006

(54) OPTICAL FLUID ANALYSIS SIGNAL REFINEMENT

(75) Inventors: Chengli Dong, Sugar Land, TX (US); Peter S. Hegeman, Houston, TX (US); Oliver C. Mullins, Ridgefield, CT (US); Kai Hsu, Sugar Land, TX (US); Andrew L. Kurkjian, Sugar Land, TX (US); Andrew J. Carnegie, Abu Dhabi (AE)

(73) Assignee: Schlumberger Technology Corporation, Sugar Land, TX (US)

( * ) Notice: Subject to any disclaimer, the term of this patent is extended or adjusted under 35 U.S.C. 154(b) by 319 days.

(21) Appl. No.: 10/249,968

(22) Filed: May 22, 2003

(65) Prior Publication Data

US 2004/0233446 A1    Nov. 25, 2004

(51) Int. Cl.
 *G01J 3/46*    (2006.01)
(52) U.S. Cl. .................. 356/402; 356/409; 356/410
(58) Field of Classification Search .............. 356/402, 356/409, 410, 432, 433, 434; 250/269.1, 250/256; 702/13; 73/152.28, 152.05, 152.06, 73/152.32
See application file for complete search history.

(56) References Cited

U.S. PATENT DOCUMENTS

| | | | |
|---|---|---|---|
| 4,609,821 A | 9/1986 | Summers | |
| 4,860,581 A | 8/1989 | Zimmerman et al. | |
| 4,936,139 A | 6/1990 | Zimmerman et al. | |
| 5,121,337 A | 6/1992 | Brown | |
| 5,145,785 A | 9/1992 | Maggard et al. | |
| 5,266,800 A | 11/1993 | Mullins | |
| 5,331,156 A | 7/1994 | Hines et al. | |
| 5,446,681 A | 8/1995 | Gethner et al. | |
| 5,739,916 A | 4/1998 | Englehaupt | |
| 6,274,865 B1 * | 8/2001 | Schroer et al. | .......... 250/269.1 |
| 6,343,507 B1 | 2/2002 | Felling et al. | |
| 6,350,986 B1 | 2/2002 | Mullins et al. | |
| 6,476,384 B1 | 11/2002 | Mullins et al. | |

OTHER PUBLICATIONS

C. Dong et al., "In-Situ Contamination Monitoring and GOR Measurement of Formation Fluid Samples," *SPE 77899, SPE Asia Pacific Oil and Gas Conference and Exhibition,* (Melbourne AU, Oct. 8-10, 2002).
O. Mullins and EY Sheu, editors, *Structures and Dynamics of Asphaltenes,* Ch. I, pp. 1-20 "Asphaltenes," and Ch. II, pp. 21-52 "Optical Interrogation of Aromatic Moieties in Crude Oils and Asphaltenes,", Plenum Press, NY NY (1998).
Badry et al., "Downhole Optical Analysis of Formation Fluids," Jan. 1994, XP-002342222, Internet URL:http://www.oilfield.slb.com/media/services/resources/oilfieldreview/ors94/0194/p21_ 28.pdf.

* cited by examiner

*Primary Examiner*—Hwa Andrew Lee
*Assistant Examiner*—Roy M. Punnoose
(74) *Attorney, Agent, or Firm*—J. L. Jennie Salazar; Victor H. Segura; Brigitte L. Echols

(57) ABSTRACT

A method for refining fluid sample data includes obtaining optical density data for a fluid sample in at least two color channels and at least one fluid component channel and determining a color-absorption function from the optical density data for the fluid sample in the at least two color channels. The method also includes calculating a portion of the optical density caused by color absorptions in each of the at least one fluid component channels, and de-coloring the optical density data in each of the at least one fluid component channels by removing the portion of the optical density data caused by color absorption.

24 Claims, 7 Drawing Sheets

OPTICAL FLUID ANALYSIS SIGNAL REFINEMENT

BACKGROUND OF INVENTION

Wells are generally drilled into the ground to recover natural deposits of hydrocarbons and other desirable materials trapped in geological formations in the Earth's crust. Once a formation of interest is reached in a drilled well, drillers often investigate the formation fluids by taking fluid samples from the formations for analysis. The analysis of a fluid sample provides information about the fluid's contents, density, viscosity, bubble point, and other important characteristics. This vital information is used for field planning decisions and for the optimization of upstream and downstream production facilities. Such fluid sampling often is done early in the life of a well to ensure that this vital information is available for field planning decisions and for developing upstream and down stream production facilities.

Typically, a fluid sample is obtained by lowering a fluid sampling tool into the well and withdrawing a fluid sample from an underground formation. One example of a sampling tool is the Modular Formation Dynamics Tester (MDT), which is a registered trademark of Schlumberger Technology Corporation, the assignee of this invention. Exemplary formation testing tools are disclosed in U.S. Pat. Nos. 4,860,581 and 4,936,139 to Zimmerman et al., which are assigned to the assignee of the present invention.

FIG. 1 shows a formation testing tool 101 designed to withdraw a fluid sample from a formation 114. The tool 101 is suspended in a borehole 110 on a wireline 115, or multiconductor cable, that is spooled from the surface. At the surface, the wireline 115 is typically connected to an electrical control system 118 that monitors and controls the tool 101.

Once at a desired depth, the tool 101 is used to obtain a formation fluid sample. The tool 101 has a probe 120, or fluid admitting means, that is selectively extendable from the tool 101, as well as an anchoring member 121 on the opposite side of the tool 101 that is also selectively extendable. The probe 120 extends from the tool 101 and seals against the borehole wall 112 so that the probe 120 is in fluid communication with the formation 114. A typical tool 101 also includes a pump (not shown). The pump is used to pump formation fluids from the formation into the tool 101. The pump may also be used to pump formation fluids from the tool 101 into the borehole 110.

One of the problems associated with fluid sampling is that the formation fluid is typically contaminated with mud filtrate. Mud filtrate is a fluid component of the drilling mud that seeps into the formation during the drilling process. The mud filtrate invades the formation and contaminates the native formation fluid near the borehole. When a fluid sample is withdrawn from the formation, the sample will initially include a significant portion of mud filtrate. Thus, in the initial stages of sample collection, the fluid sample is not representative of the native formation fluids.

To solve this problem, a fluid sample typically is withdrawn from the formation and pumped into the borehole or into a large waste chamber in the sampling tool until the fluid being withdrawn has been "refined" or "cleaned up." A "refined" or "cleaned up" sample is one where the concentration of mud filtrate in the fluid sample is acceptably low so that the fluid represents the native formation fluids. At that point, a sample may be collected for later analysis.

Referring to FIG. 1 again, formation fluid is withdrawn from the formation 114 by the probe 120, and the fluid passes through a fluid analyzer 125 before it is pumped out of the tool 101 and into the borehole by a pumping means (not shown). The fluid analyzer 125 analyzes the fluid sample to determine the level of mud filtrate contamination. Once the formation fluid being withdrawn through the probe has cleaned up, a fluid sample may be taken by pumping the fluid sample into one of the sample chambers 122, 123.

One type of fluid analyzer used in a formation testing tool is an optical sensor, which measures the'optical density ("OD") of the fluid sample at several different wavelengths in the near-infrared ("NIR") and visible light spectra. The OD is calculated from the transmittance, which is a ratio of the transmitted light to the incident light. The OD typically is calculated as $OD=-\log_{10}(T)$, where T is the transmittance. The oil used in an oil-based mud ("OBM") typically is light in color, thus, as the fluid sample cleans up, the OD at the color channels increases asymptotically to the OD of the darker native formation fluid. For water based mud ("WBM") the mud filtrate is usually colorless, thus, as the fluid sample cleans up, the OD at the color channels increases asymptotically to the OD of the darker native formation fluid.

Two types of absorption contribute to the OD of a fluid sample: color absorption and molecular vibration absorption. Color absorption occurs when incident light interacts with orbital electrons. Oils may exhibit different colors because they have varying amounts of aromatics, resins, and asphaltenes, each of which absorb light in the visible and NIR spectra. For example, heavy oils have higher concentrations of aromatics, resins, and asphaltenes, which give them dark colors. Light oils and condensate, on the other hand, have lighter, yellowish colors because they have lower concentrations of aromatics, resins, and asphaltenes.

Molecular vibration absorption is the absorption of a particular frequency of light due to resonance of the chemical bonds in a molecule. While color absorption covers the visible and NIR spectrums, molecular vibration absorption occurs only at specific wavelengths for specific materials. For any given molecule, the wavelength at which vibration absorption occurs is related to the molecular structure and the types of chemical bonds in the fluid sample. For example, most oils have molecular vibration absorption peaks near wavelengths of 1,200 nm, 1,400 nm, and 1,700 nm.

Another factor that can affect the measured OD of a fluid sample is known as "scattering." Scattering is when the incident light is reflected by particles in the fluid sample so that the reflected light does not reach the detector. Typically, scattering occurs independent of the wavelength of the incident light, but there are some circumstances where scattering may depend on the wavelength of light.

Molecular vibration absorption is a function of the concentration of the particular substance, and it is not necessarily affected by the phase of the substance. For example, the methane absorption resonance peak (near 1,670 nm) will have about the same magnitude, regardless of whether the methane is in the gas phase or dissolved in the oil.

FIG. 2 shows the OD of several types of oil, including condensate 202, black oil 204, and tar 206. The OD of these fluids due to color is wavelength dependent and forms a continuous curve over the wavelength spectrum. The OD for the oils shown in FIG. 2 also have molecular vibration absorption peaks 212, 214, 216 at specific wavelengths. Where the OD due to color is a continuous curve over the spectrum, the OD due to molecular vibration absorption occurs only at discrete wavelengths. As shown in FIG. 2, crude oils have molecular vibration absorption peaks at about 1,200 nm (shown at 212), at about 1,400 nm (shown at 214), and at about 1,700 nm (shown at 216).

One type of optical sensor is the Optical Fluid Analyzer ("OFA"), which is a trademark of Schlumberger Corporation, the assignee of the present invention. The OFA measures the OD of the fluid sample at ten different wavelengths in the NIR and visible ranges. When fluid is first withdrawn from a formation, the fluid sample is composed mostly of light colored OBM filtrate or WBM filtrate. As the fluid sample cleans up, the fluid sample will contain more of the darker native formation fluid. The OD of the fluid sample in color channels will change as the fluid cleans up. For example, because the formation fluid is darker in color than a typical OBM filtrate, the OD of the fluid sample at the color channels will increase as the fluid sample is withdrawn. The OD at the color channels will asymptotically approach the OD of the formation fluid.

By taking OD data at multiple times, the OD of the native formation fluid, called the "contamination free" OD, can be mathematically determined by computing the asymptotic value of the measured OD. "Contamination free OD" means the OD of the fluid sample when there is no contamination in the sample, (i.e., the OD of the formation fluid). Once the contamination free OD is predicted, the amount of OBM filtrate contamination in the fluid sample may be determined based on the measured OD and the contamination free OD. Methods for determining the contamination of OBM in a fluid sample are disclosed, for example, in U.S. Pat. No. 5,266,800 to Mullins, which is assigned to the assignee of the present invention.

Another type of optical sensor is called the Live Fluid Analyzer ("LFA"), which is a Trademark of Schlumberger Corporation, the assignee of the present invention. The LFA is different from the OFA because the LFA includes a methane channel at the wavelength of a "methane peak". Both the LFA and OFA have an oil channel at the wavelength of an "oil peak." A "methane peak" is a molecular vibration absorption peak of methane, whose wavelength corresponds to the resonance of the CH bond in a methane molecule. One methane molecular vibration absorption peak occurs at a wavelength of about 1,670 nm. The molecular vibration absorption occurs independently of the color of the fluid and independently of whether the methane is in the gas phase or dissolved in the formation fluid. Similarly, an "oil peak" is a molecular vibration absorption peak of oil, whose wavelength corresponds to the resonance of the combination of $CH_2$ and $CH_3$ groups in an oil molecule. The oil peak typically is at a wavelength of about 1,720 nm.

Typically, OBM filtrate contains negligible amounts of methane, so the OD at the methane peak will increase as the fluid sample is withdrawn from the formation. The OD of the methane peak will asymptotically approach the OD at the methane peak of the formation fluid. The percent contamination of the fluid sample may be determined by monitoring the OD in the methane channel and comparing it to the asymptotic value.

Another formation fluid property that may be calculated using a methane channel is the gas oil ratio ("GOR"). The GOR is the ratio of the volume of hydrocarbons in the gaseous phase in the native formation fluids over the volume of liquid hydrocarbons at standard conditions. The GOR is important in the design of the upstream and downstream production facilities. For example, if the GOR is high, the surface facilities must be designed to handle a large amount of gas from the well. One method for calculating the GOR is disclosed in U.S. Pat. No. 6,476,384 to Mullins, et al., incorporated by reference in its entirety, which is assigned to Schlumberger Technology Corporation, the assignee of the present invention.

Another type of optical sensor is called the Condensate and Gas Analyzer ("CGA"), which is a Trademark of Schlumberger Corporation, the assignee of the present invention. A CGA uses optical channels at specific frequencies to get a better estimate of the spectrum of gases and liquids present in a fluid sample. For example, a typical CGA has a channel that corresponds to the resonance peak for molecular vibration absorption in carbon dioxide. A typical CGA is able to determine mass concentrations of methane, non-methane gaseous hydrocarbons, carbon dioxide, and liquid hydrocarbons.

While these analyzers provide convenient methods for monitoring various components in formation fluids and, hence, the extent of the mud filtrate contamination in the formation fluids, they may still be affected by the color of the fluid sample, the amount of water present in the fluid sample, and any particles in the fluid sample that scatter the incident light used to measure the OD. It is desirable to have methods that remove the effects of color, water, and scattering.

SUMMARY OF INVENTION

In some embodiments, the invention relates to methods for refining fluid sample data including obtaining optical density data for a fluid sample in at least one color channel and at least one fluid component channel, and determining a color-absorption function from the optical density data. The method also includes calculating a portion of the optical density caused by color absorptions in the at least one fluid component channels, and de-coloring the data by subtracting the portion of the optical density in the at least one fluid component channels caused by color absorptions.

In other embodiments, the invention relates to methods for refining fluid sample data including obtaining optical density data for a fluid sample in a water channel and in at least one fluid component channel and calculating a portion of the optical density caused by water absorptions of the at least one component channel based on an optical density in the water channel and a water-absorption ratio for the at least one component channel. The methods next include de-watering the optical density in each of the at least one fluid component channels by removing the portion of the optical density data caused by water absorptions.

In some embodiments, the invention relates to methods for refining fluid sample data including obtaining optical density data for a fluid sample in at least one color channel, a water channel, and at least one fluid component channel and determining a color-absorption function from the data. The methods then include calculating a portion of the optical density caused by color absorptions in the at least one fluid component channels, and de-coloring the optical density data in the at least one fluid component channel by removing the portion of the optical density caused by color absorptions.

Methods according to these embodiments may also include calculating a portion of the optical density caused by water absorptions of the at least one component channel based on an optical density in the water channel and a water-absorption ratio for the at least one component channel, and de-watering the optical density data in the at least one fluid component channel by removing the portion of the optical density caused by the water absorptions.

In some embodiments, the invention relates to methods for refining fluid sample data including obtaining optical density data for a fluid sample in a plurality of optical channels, developing a system of equations that model the optical density in the plurality of optical channels as a sum of at least two of the group consisting of color absorptions, molecular vibration absorptions, water absorptions, and scattering, and solving the system of equations to determine the molecular vibration absorptions in at least a methane channel and an oil channel at each of the plurality of times.

In certain embodiments, the invention relates to an electronics system that includes an input device adapted to receive optical density data for a fluid sample at a plurality of times, and a memory operatively coupled with the input device to store the received data. The electronics system may also include a processor operatively coupled to the memory and adapted to use the optical density data to develop a system of equations that model the optical density in each of the plurality of optical channels as a sum of at least two of the group consisting of color absorptions, molecular vibration absorptions, water absorptions, and scattering, and adapted to solve the system of equations to determine the molecular vibration absorptions in a methane channel and an oil channel.

DETAILED DESCRIPTION

In certain embodiments, the present invention relates to methods for refining, or cleaning up, a signal from a downhole optical fluid analyzer. In some embodiments, the invention relates to removing a color effect. In other embodiments, the invention relates to removing a water effect. In other embodiments, the invention relates to removing a scattering effect. In one or more embodiments, the invention relates to simultaneously removing color, water, and scattering effects.

De-Colorization

Figure 3:
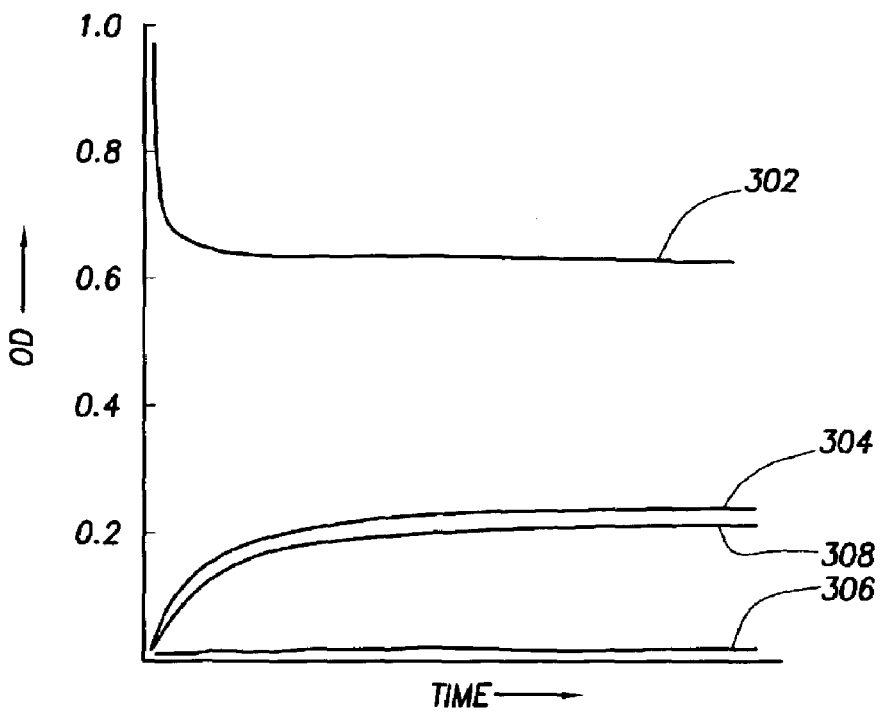
FIG. 3 shows a graph of the OD in several channels of an optical sensor versus time.

FIG. 3 shows a graph of the OD of a light-colored oil at several channels in an OBM situation. The plot shows a methane channel (shown at plot 304), an oil channel (shown at plot 302), and a base channel (shown at plot 306). A "methane difference" channel, which is the base channel subtracted from the methane channel, is also shown (plot 308). The base channel (plot 306), which does not contain molecular vibration absorptions of methane or oil, is used as a baseline. The methane difference typically is used because spurious reading that are common to both the methane channel and the base channel are eliminated.

The methane difference (plot 308) builds up with time to an asymptotic value. This buildup of the methane difference (plot 308) may be used to predict the contamination and, in connection with the oil channel, to predict the gas oil ratio of the formation fluid. Because FIG. 3 represents an example of OD data collected from light oil, it shows typical behavior of the methane, oil, and base channels without any effect from color.

The "contamination" of a fluid sample refers to the amount of mud filtrate in a fluid sample. Typically, the contamination is reported as a percent contamination by volume. The gas oil ratio ("GOR") is the ratio of the volume of gas to the volume of liquid in a fluid sample at standard conditions.

Figure 1:
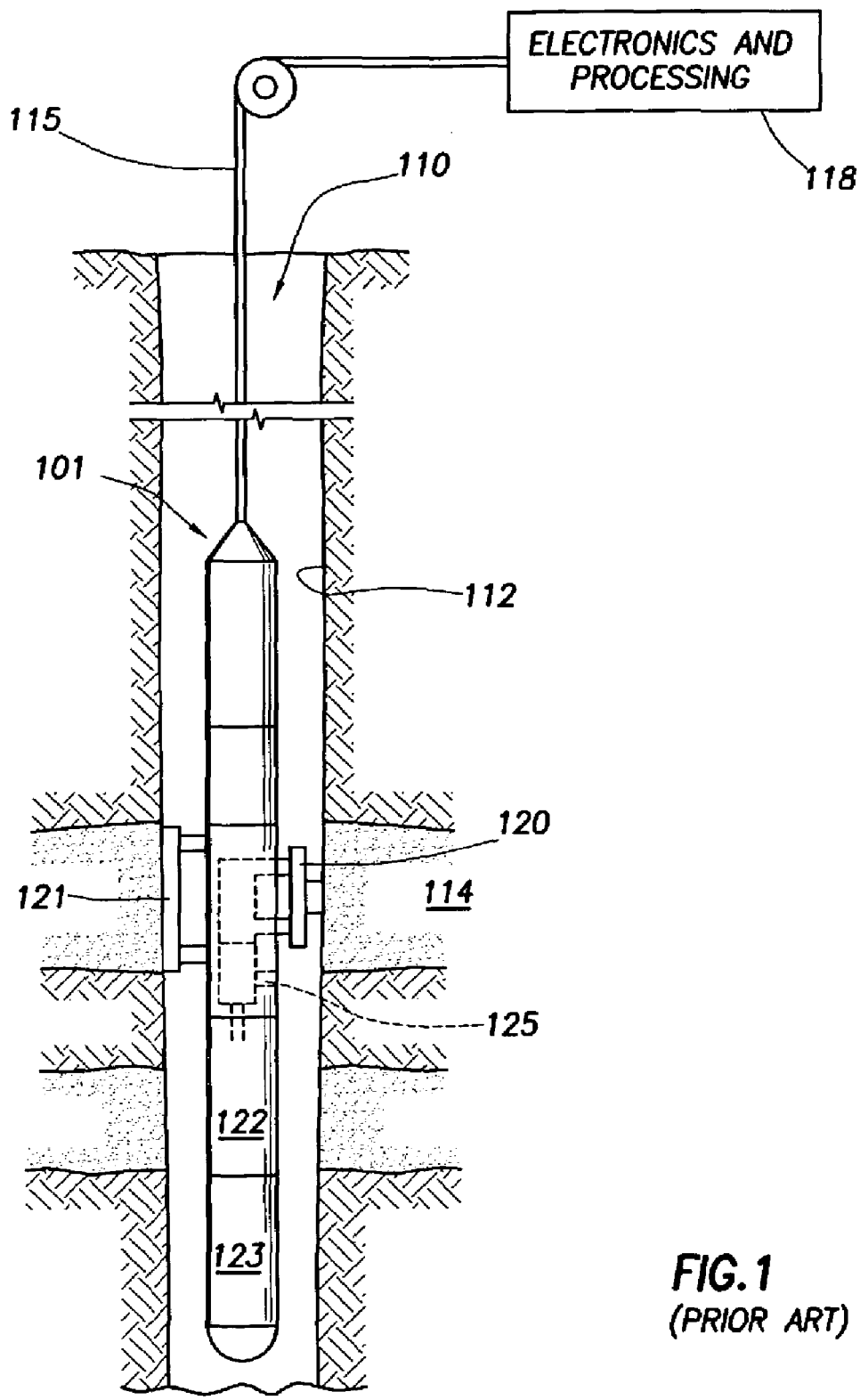
FIG. 1 shows a cross-section of a prior art formation testing tool.
Figure 2:
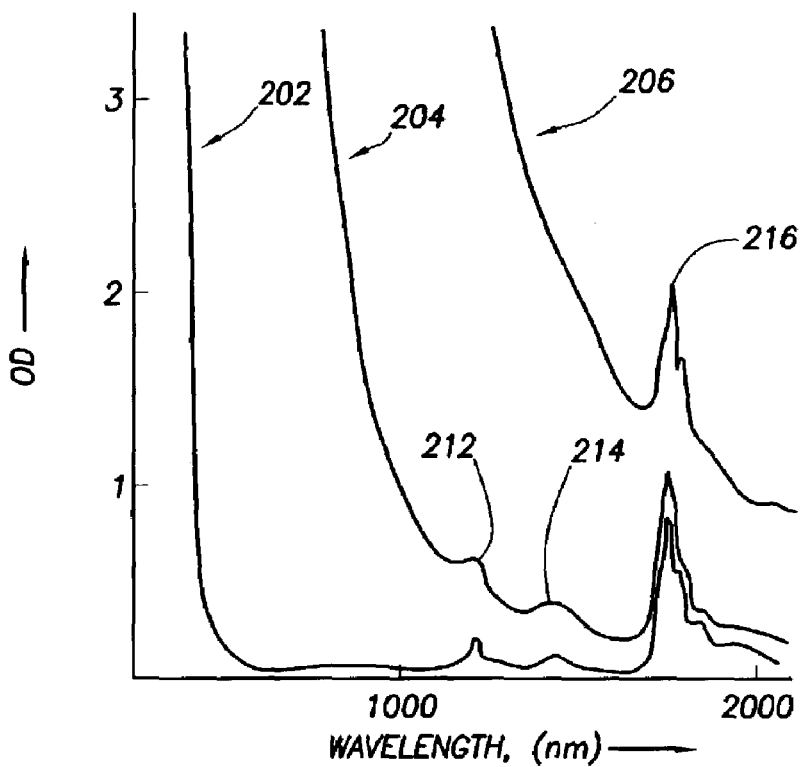
FIG. 2 shows a graph of the OD of several types of oil versus the wavelength of the incident light.

When a fluid sample contains very dark oil, color absorption occurs in all of the channels, including the methane and oil channels. As can be seen in FIG. 2, black oils (shown at 204) and tars (shown at 206) have significant color absorption near 1,700 nm, which is near a molecular absorption peak (shown at 216) for the methane and oil channels. As a result, the methane and oil channels can be significantly affected by a dark oil.

Figure 4:
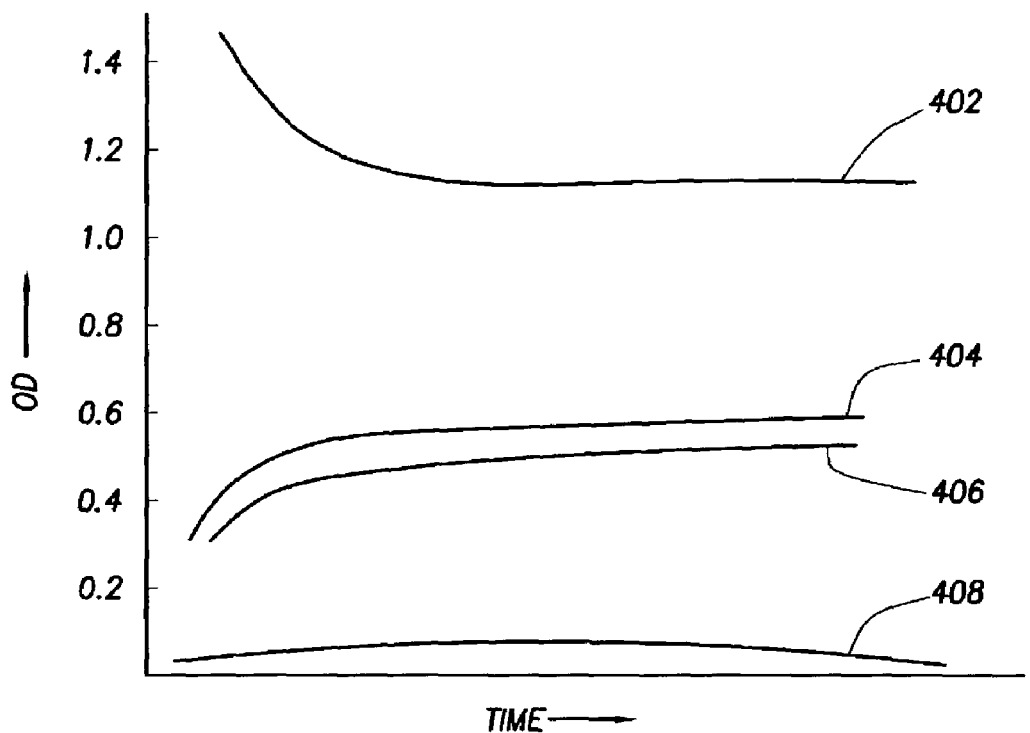
FIG. 4 shows a graph of the OD in several channels of an optical sensor for a dark oil versus time.

This "color effect" is shown in FIG. 4. The OD in the oil channel (shown in plot 402) is elevated (compared to FIG. 3) because it contains both the molecular vibration absorption at the oil peak and the color absorption from the dark oil. Similarly, the OD in the methane channel (shown at plot 404) is elevated because it represents both molecular vibration absorption in the methane peak and color absorption from the dark oil. The color effect also significantly increases the OD in the base channel (shown at plot 406). While the base channel in FIG. 3 (shown at plot 306) is close to zero, FIG. 4 shows that the color effect can significantly increase the OD in the base channel (shown at plot 406).

The color effect causes the methane difference (shown at plot 408) to have a very low OD, and, as can be seen in FIG. 4, it may be flat or even decreasing. Such a methane difference plot provides for a zero contamination prediction, even though there may be significant contamination in the fluid sample. Further, because the GOR is determined from the ratio of the methane channel over the oil channel, elevated methane, oil, and base channels create inaccuracies in the GOR prediction.

To accurately predict contamination and GOR, the color effect must be removed from the methane, oil, and base channels. As shown in FIG. 2, the color absorption is wavelength dependent. Equation 1 shows this relationship:

$$OD = \alpha L e^{\beta/\lambda} \qquad \text{Eq. 1}$$

where OD is the optical density, $\alpha$ and $\beta$ are constants, L is the path length, and $\lambda$ is the wavelength. Equation 1 is one example of a "color-absorption function." A color-absorption function." A color-absorption is any function that defines the OD of a fluid sample caused by color absorptions. In some embodiments, a color-absorption function is wavelength dependent. In other embodiments, the color-absorption function may be a constant. Taking the natural log of both sides of Equation 1 yields:

$$\ln(OD) = \ln(\alpha L) + \beta/\lambda \qquad \text{Eq. 2}$$

Figure 5:
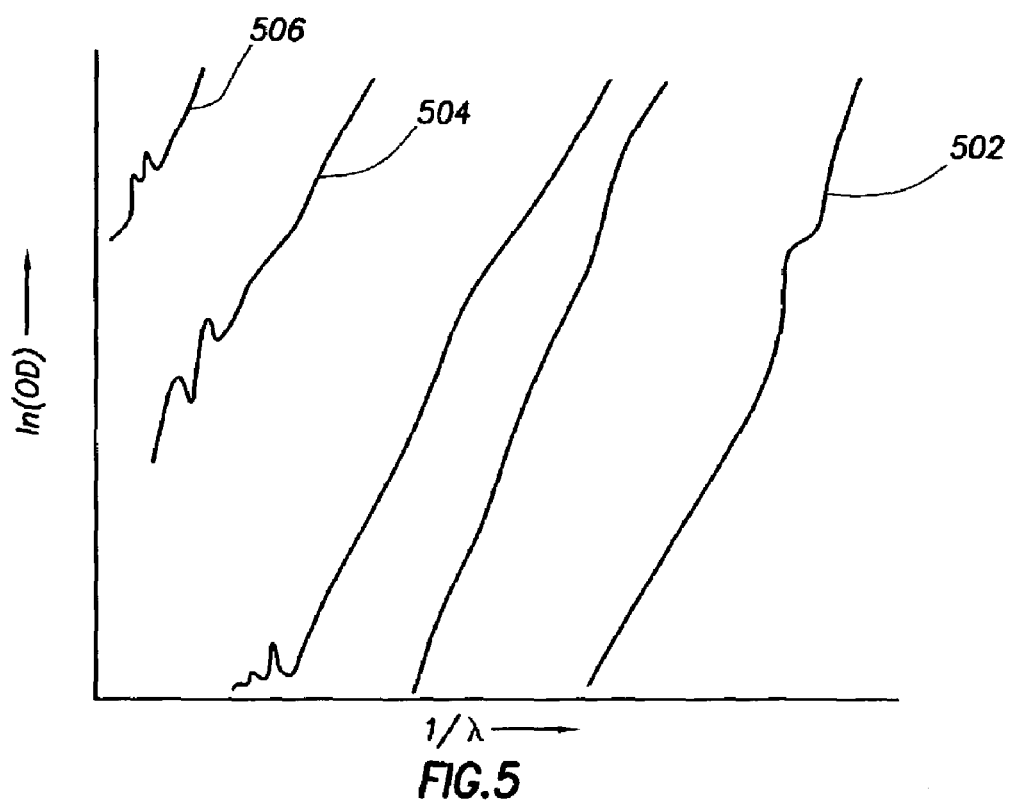
FIG. 5 shows a graph of the natural log of the OD for several types of oil versus the reciprocal of wavelength.

Equation 2 shows that, for crude oils, the natural log of the OD has a linear relationship with the reciprocal of the wavelength. This relationship is shown in FIG. 5. The plots of ln(OD) v. $1/\lambda$ for crude oils over a range of darkness are shown. Specifically, the gas condensate plot 502, the black oil plot 504, and the tar plot 506 all demonstrate the linear relationship. This relationship may be used to predict the color absorption at any wavelength based on the color absorption at known wavelengths.

Typically, an LFA sensor has five color channels. A "color channel" is a channel that senses the OD of a fluid sample at a wavelength where the measured OD is primarily due to color absorption. Data from color channels may be used with Equations 1 and 2 to determine the constants, $\alpha$ and $\beta$. Although no specific curve-fitting techniques are described herein, those having ordinary skill will be familiar with curve-fitting techniques that may be used with the invention. Further, the number of color channels in a given tool or type of tool may vary, and the number is not intended to limit the invention. The LFA tool is used only as an example.

Once the constants, $\alpha$ and $\beta$ are determined, Equation 1 may be used to predict color absorption at other wavelengths. The color absorption in the methane channel, the oil channel, and the base channel may be subtracted from the measured overall OD in those channels. The remaining OD in, for example, the methane channel, better represents the molecular vibration absorption caused by the methane present in the fluid sample.

Figure 6:
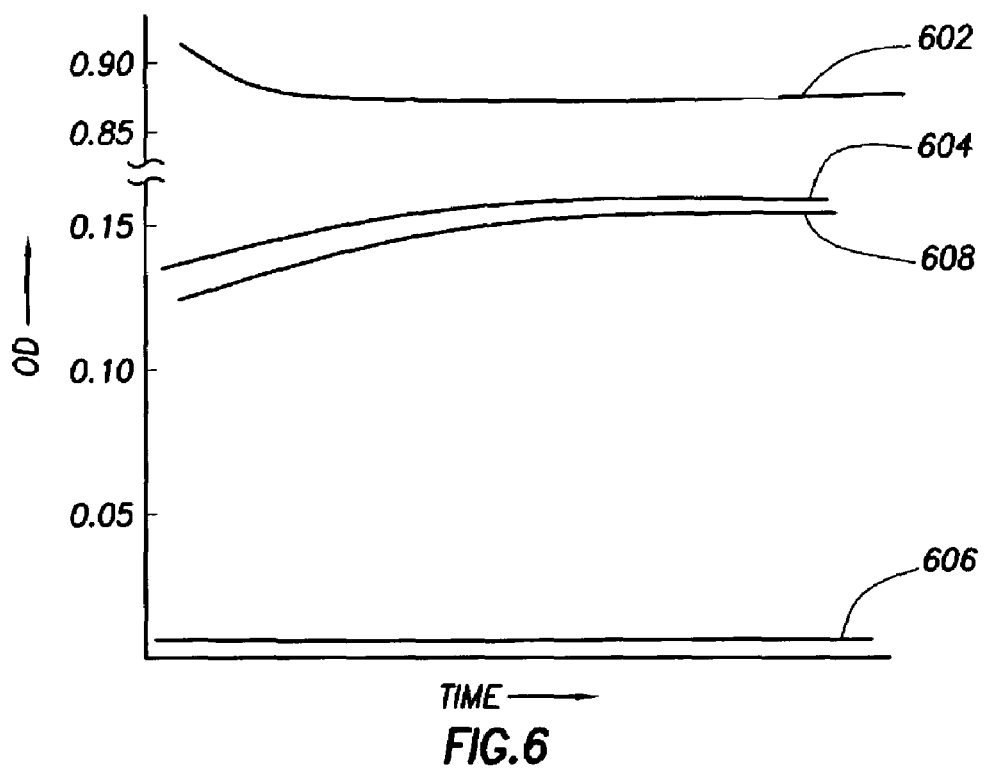
FIG. 6 shows a graph of the color-corrected OD in several channels of an optical sensor for a dark oil versus time.

Measuring the color absorption in color channels enables the prediction of the color absorption at other wavelengths or in other channels. An example of an embodiment for applying a de-coloring algorithm to the data in FIG. 4 is shown in FIG. 6. The OD in the methane channel (shown at plot 604) and the OD in the base channel (shown at plot 606) are significantly reduced because the color absorption effects have been removed. The OD in the oil channel (shown at plot 602) is also significantly reduced as a result of the de-coloring algorithm. As can be seen in FIG. 6, the color-corrected methane channel plot 604 builds up to an asymptotic value. The color-corrected base channel plot 606 is almost zero, indicating that most of the OD in the base channel plot (406 in FIG. 4) was due to color absorption. The color-corrected methane difference plot 608, like the color-corrected methane channel plot 604, shows a buildup that may be used to predict contamination, and the color-corrected methane, oil, and base channels may be used to predict GOR.

Those having ordinary skill in the art would realize that the de-coloring algorithm may be applied to channels other than the oil channel and the methane channel. Any fluid component channel can be de-colored using embodiments of this invention. A "fluid component channel" is any channel that can be used to determine the composition of a fluid sample or a property of a fluid sample. For example, some downhole fluid sampling tools include an optical sensor with a channel that responds to non-methane gaseous hydrocarbons. Such a channel may be de-colored using certain embodiments of the present invention.

Figure 10:
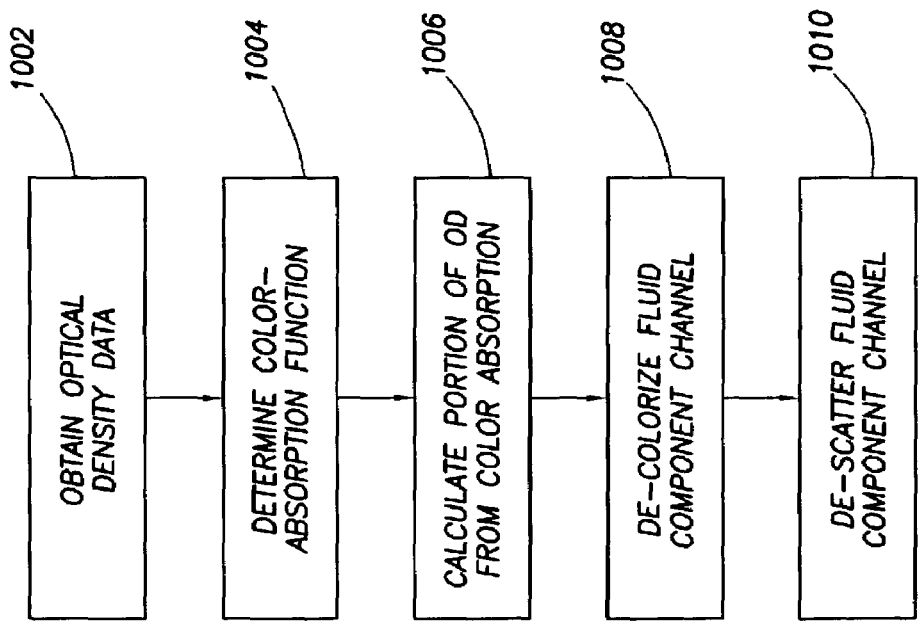
FIG. 10 shows one embodiment of a method according to the invention.

FIG. 10 shows a method according to certain embodiments of the invention. The method first includes obtaining data related to the OD of a fluid sample ("optical density data") in at least one color channel and in at least one fluid component channel (shown at step 1002). In this description, "optical density data" is generally used to refer to data related to optical density or transmittance. In some embodiments, OD data is obtained for two color channels. In some embodiments, the data is collected at a plurality of times during the sampling process. In some embodiments, the corrections are applied at a plurality of times during the sampling process. The data may comprise the OD in the desired channels, or it may comprise another type of data that is related to the OD, such as a transmittance value. Also, in some embodiments, the data is obtained by measurement, while in some other embodiments, the data comprises previously measured data, and it is obtained from storage media. In some embodiments, the at least one fluid component channel comprises a methane channel and an oil channel.

The method next includes determining a function of wavelength for the OD of the fluid sample due to color absorptions from the optical density data for the at least one color channel (shown at step 1004). In some embodiments, such a function ("color-absorption function") is determined at each of the plurality of times. One example of such a function is shown in Equation 1. The data from at least one color channel may be used to determine the constants in the general form of any equation selected for the color absorptions.

It is noted that Equation 1 contains two unknowns that must be determined, but the invention is not limited to two unknowns. For example, a color-absorption function may estimate or assume one of the values. Such a color-absorption function would contain only one unknown that could be determined using data from only one color channel. Further, those having ordinary skill in the art may be able to devise a color-absorption function that includes more than two unknowns. A typical fluid analyzer includes five color channels, enabling the determination of more than two unknowns. The invention is not limited by the form of the color-absorption function.

The method then includes calculating the portion of the OD in the at least one fluid component channel that is caused by color absorptions (shown at step 1006). In some embodiments, the portion of the OD caused by color absorptions is calculated at each of the plurality of times. In other embodiments, the method includes determining the portion of the OD in the base channel that is caused by color absorptions.

The method next includes de-colorizing the data by subtracting the portion of the OD in each of the at least one fluid component channels that is caused by color absorptions (shown at step 1008). In some embodiments, this is done at each of the plurality of times. In some embodiments, the method also includes de-scattering the at least one fluid component channel by de-colorizing the base channel and subtracting the de-colored OD from a base channel from the de-colored OD in each of the at least one fluid component channels (shown at step 1010), as will be described below.

De-Watering Algorithm

Figure 7:
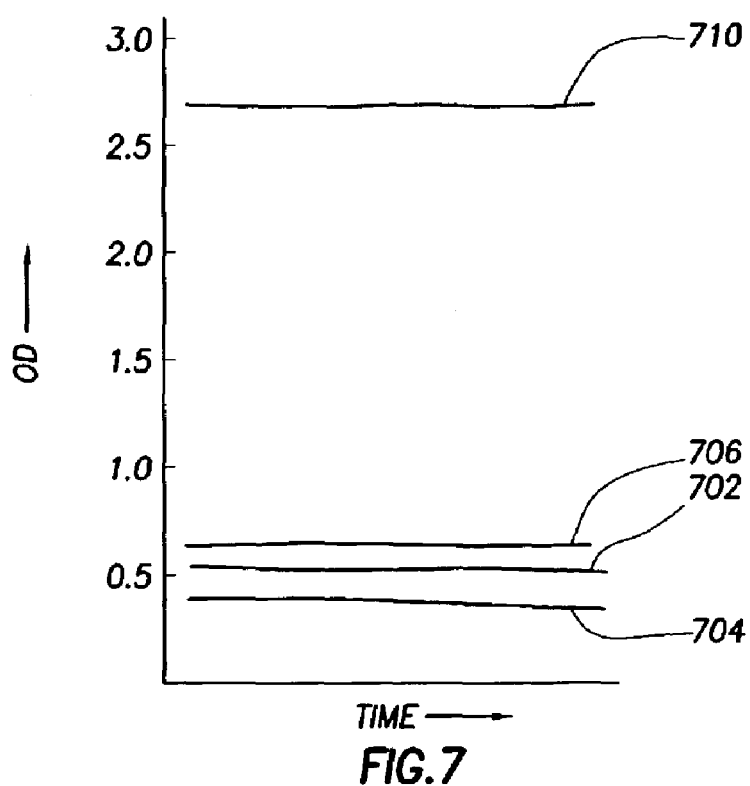
FIG. 7 shows a graph of the OD due to water absorptions in several channels.

Water in a fluid sample may have an impact on the OD measured in all of the channels. This "water effect" can become significant in wells drilled with a water-based mud and in wells drilled through formations that contain native water. FIG. 7 shows the water effect based on a fluid sample comprised entirely of water. A "water channel" (shown at plot 710) operates at a wavelength that corresponds to a molecular vibration absorption peak for water. As shown, water in a sample fluid may also significantly increase the OD in the base channel (shown at plot 706), the oil channel (shown at plot 702), and the methane channel (shown at plot

704). The water effect is more pronounced in the oil and base channels (shown at plots 702, 706) than it is in the methane channel (shown at plot 704). Because of this, even small amounts of water in a fluid sample can have a profound effect on the accuracy of contamination and GOR predictions that rely on an accurate OD measurement in the methane channel.

The water absorptions in all of the channels are related to the mass percentage (henceforth referred to as partial density) of water in the fluid sample. That is, effect of water absorptions on the OD increases with the amount of water or the density of water in the fluid sample. Another feature of water absorptions is that the ratios of water absorptions between different channels remains almost constant at any water density. Thus, by using a water channel that has absorptions only from water, the water absorptions in all other channels may be computed.

For example, in some embodiments, the water absorptions in the methane channel are about 17.2% of the water absorptions in the water channel. The water-absorption ratio in the methane channel is 0.172. Thus, $OD_{methane}=0.172\ OD_{water}$. Similarly, in some embodiments, the water absorptions in the oil channel are about 18.7% of the water absorptions in the water channel (water-absorption ratio=0.187), and the water absorptions in the base channel are about 22.8% of the water absorptions in the water channel (water-absorption ratio=0.228) ($OD_{oil}=0.187\ OD_{water}$; $OD_{base}=0.228\ OD_{water}$). It is noted that the ratios of the water absorptions in the various channels to that of the water channel are determined through experimentation. The particular values may change, depending on the specific wavelengths used in each channel. Also, different methods for determining the ratios may yield slightly different results. The present invention is not intended to be limited by the values of the water-absorption ratios.

At each time level, the algorithm includes measuring the OD in the water channel, computing the water absorptions in the methane, oil, and base channels based on the experimentally determined ratios, and subtracting the water absorptions from each channel. It is noted that the water effect can be removed from any channel, not only the methane, oil, and base channels.

Figure 8:
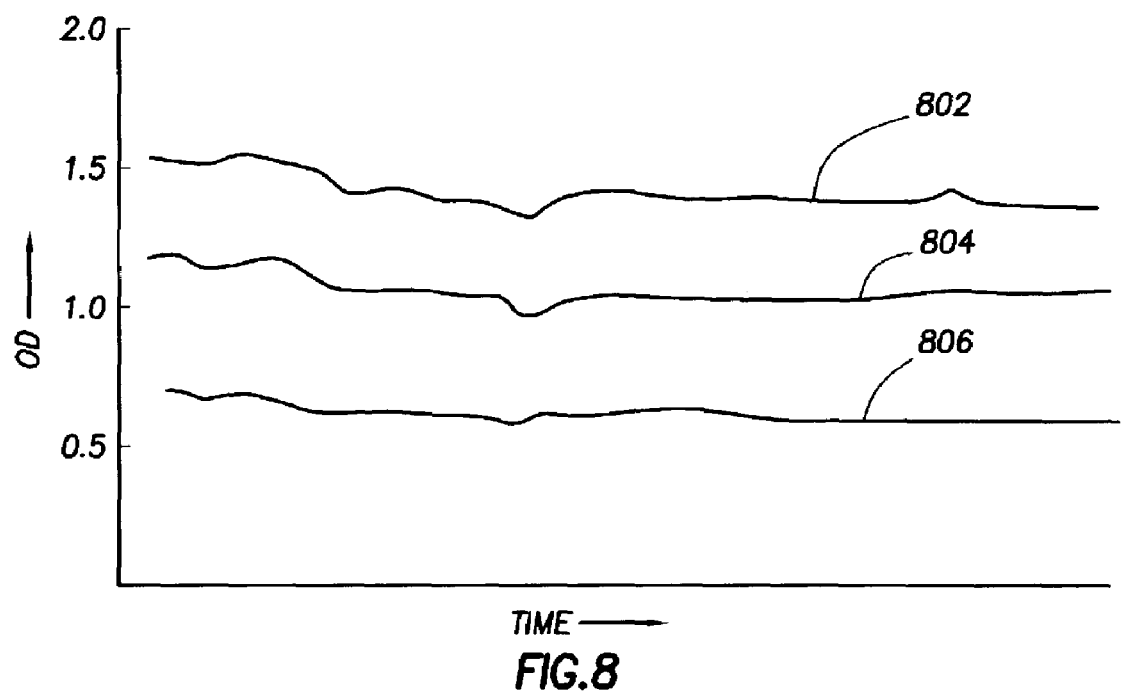
FIG. 8 shows a graph of the OD in several channels of an optical sensor for a fluid sample containing water versus time.

FIG. 8 shows plots of an oil channel (shown at 802), a methane channel (shown at 804), and a base channel (shown at 806) from a fluid sample taken from a well drilled with a water-based mud. The plots in FIG. 8 are taken after a period of time has elapsed, so the initial buildup is not seen and the lines are relatively flat. Nonetheless, as can be seen in FIG. 8, the changing water content in the fluid sample causes fluctuations in the OD measured in the channels.

Figure 9:
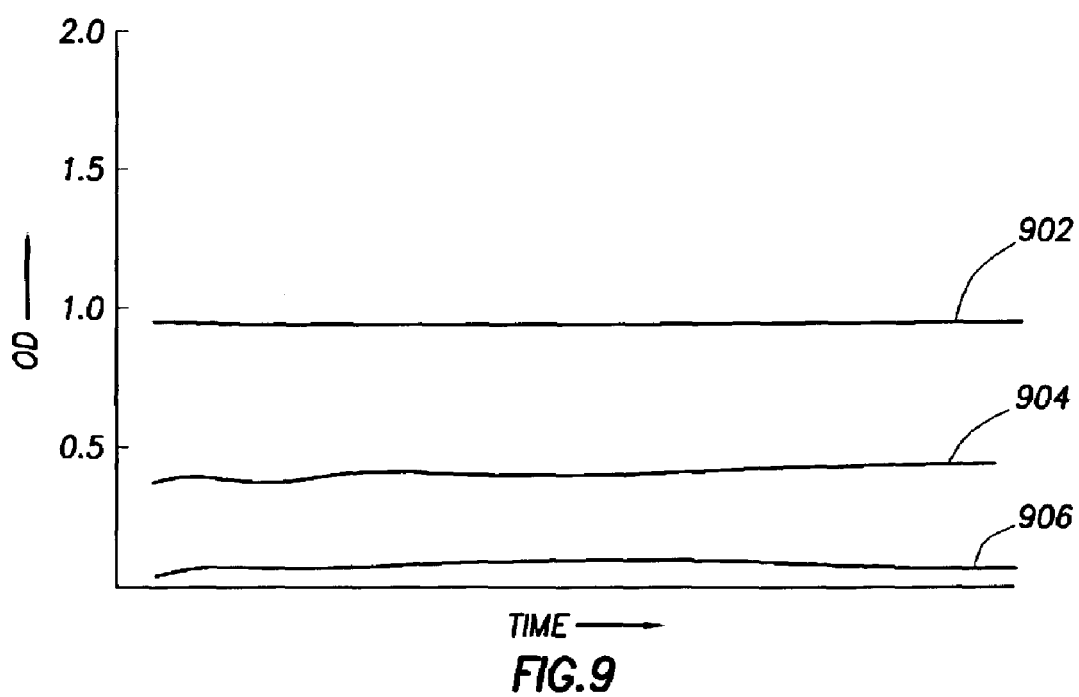
FIG. 9 shows a graph of the water-corrected OD in several channels of an optical sensor for a fluid sample containing water versus time.

FIG. 9 shows plots of an oil channel (shown at 902), a methane channel (shown at 904), and a base channel (shown at 906), similar to FIG. 8, but after the water effect has been removed by subtracting the water absorptions from each channel. The plots 902, 904, and 906 have significantly less fluctuation than before the de-watering algorithm is performed. This improves the accuracy of contamination and GOR predictions.

Figure 11:
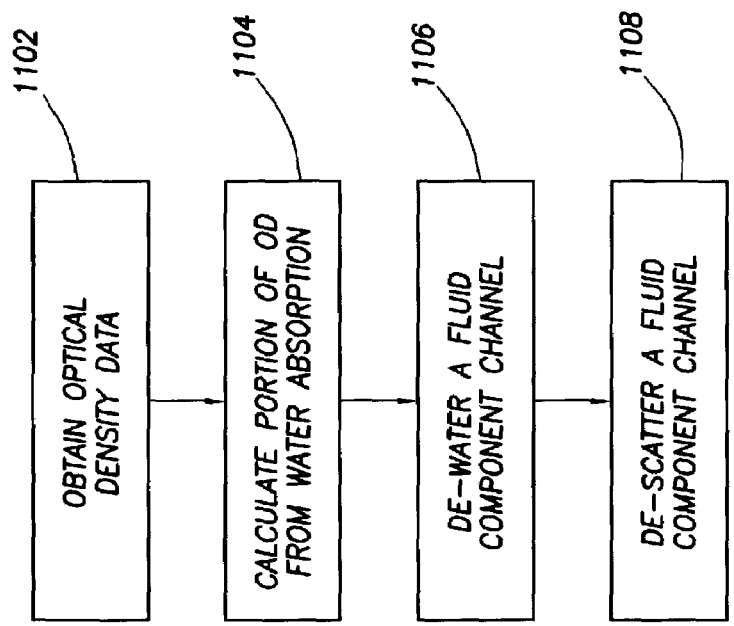
FIG. 11 shows one embodiment of a method according to the invention.

FIG. 11 shows a method according to certain embodiments of the invention. The method first includes obtaining data related to the OD of a fluid sample in a water channel and in at least one fluid component channel (shown at step 1102). In some embodiments, the data is collected at a plurality of times during the sampling process. The data may comprise the OD in the desired channels, or it may comprise another type of data that is related to the OD, such as a transmittance value. Also, in some embodiments, the data is obtained by measurement, while in some other embodiments, the data comprises previously measured data, and it is obtained from storage media. In some embodiments, the at least one fluid component channel comprises the methane channel and the oil channel.

The method next includes calculating the portion of the OD in the fluid component channels that is caused by water absorptions (shown at step 1104). In some embodiments, this calculation is based on the OD in the water channel and a water-absorption ratio. In some other embodiments, the method includes determining the portion of the OD in the base channel that is caused by water absorptions.

The method next includes de-watering the data by subtracting the portion of the OD in each of the fluid component channels that is caused by water absorptions (shown at step 1106). In some embodiments, this is done at each of the plurality of times. In some embodiments, the method also includes de-scattering the at least one fluid component channel by de-watering the base channel and subtracting the de-watered OD from the base channel from the de-watered OD in the at least one fluid component channel (shown at step 1108), as will be described below.

De-Scattering Algorithm

Scattering is usually caused by fine particles in a fluid sample that redirect some of the incident light so that it does not reach the detector. It is assumed that scattering is wavelength independent; that is, it affects all channels in the same way. In most cases, the scattering effect may be removed by subtracting the base channel from the methane channel and oil channels before they are used to predict contamination or GOR. It is noted that the base channel may be de-colored or de-watered before the methane and oil channels are de-scattered.

General Algorithms

The above algorithm descriptions are for stand-alone algorithms to remove the color effect, the water effect, and the scattering effect. In many cases, however, two or three of these effects are present and must be simultaneously removed from OD data for a fluid sample.

Figure 12:
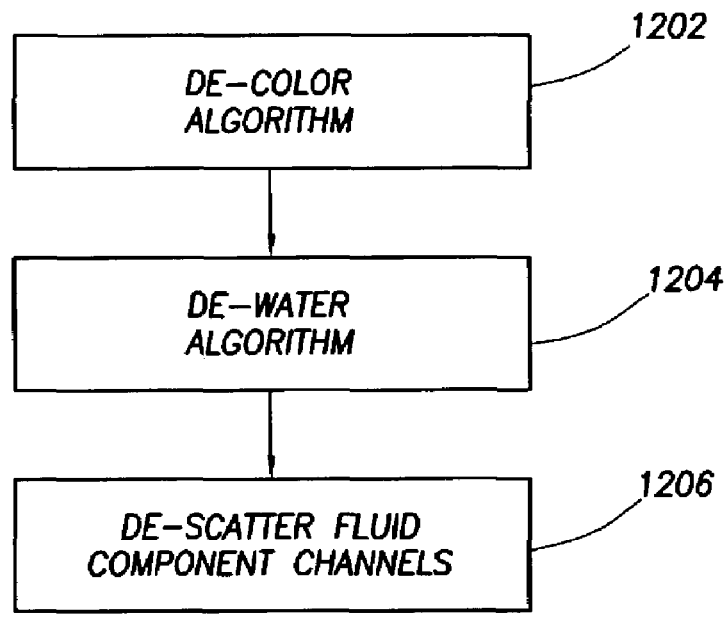
FIG. 12 shows one embodiment of a method according to the invention.

In some embodiments, the stand-alone algorithms are used sequentially to remove the color, water, and scattering effect. FIG. 12 shows one embodiment of the first general algorithm, as it is applied to each time level. First, the stand-alone de-coloring algorithm is used to remove the color effect, or decolorize, the channels (shown at step 1202). This may be done, for example, as is shown in FIG. 10. Next, FIG. 12 shows that the de-watering algorithm is used to remove the water effect from the methane, oil, and base channels (shown at step 1204). This may be done, for example, as is shown in FIG. 11. Finally, FIG. 12 shows that the de-scattering algorithm may be used to remove the scattering effect from the methane and oil channels (shown at step 1206). This may be done by subtracting a de-colored and de-watered base channel from the de-colored and de-watered methane and oil channels.

Those having ordinary skill in the art will realize that certain embodiments of the invention may not include all of the steps shown in FIG. 12. Any one of the three stand-alone algorithms could be omitted. For example, if a fluid sample is taken from a formation that contains only light oil or gas condensate, the de-coloring algorithm (shown at step 1202) may be omitted. Further, the invention is not limited by the order in which the individual stand-alone algorithms are performed. For example, in some embodiments, the de-watering algorithm (shown at step 1204) is performed first, followed by the de-coloring and the de-scattering algorithms. The invention is not intended to be limited by the order in which the stand-alone algorithms are performed.

In other embodiments, the color effect, the water effect, and the scattering effect are simultaneously removed from all channels at each time level. In some embodiments, this is accomplished by establishing a mathematical model for the OD in each channel. Equations 3–12 show the OD in each of ten channels in an exemplary LFA tool. The equations represent a color absorption, a water absorption, a scattering, and methane and oil absorptions for each channel. For the LFA tool, channels 1–5 are color channels, channel 6 is water channel, channel 7 is base channel, channel 0 is methane channel, channel 8 is oil channel, and channel 9 has absorptions from all of water, methane and oil.

A system of equations can be developed that model the absorption in every channel:

$$OD_1 = \alpha L e^{\beta/\lambda_1} + s - 0.020w \quad \text{Eq. 3}$$

$$OD_2 = \alpha L e^{\beta/\lambda_2} + s - 0.021w \quad \text{Eq. 4}$$

$$OD_3 = \alpha L e^{\beta/\lambda_3} + s - 0.020w \quad \text{Eq. 5}$$

$$OD_4 = \alpha L e^{\beta/\lambda_4} + s - 0.015w \quad \text{Eq. 6}$$

$$OD_5 = \alpha L e^{\beta/\lambda_5} + s + 0.022w + p \quad \text{Eq. 7}$$

$$OD_6 = \alpha L e^{\beta/\lambda_6} + s + w + q \quad \text{Eq. 8}$$

$$OD_7 = \alpha L e^{\beta/\lambda_7} + s + 0.228w \quad \text{Eq. 9}$$

$$OD_0 = \alpha L e^{\beta/\lambda_0} + s + 0.172w + A \quad \text{Eq. 10}$$

$$OD_8 = \alpha L e^{\beta/\lambda_8} + s + 0.187w + B \quad \text{Eq. 11}$$

$$OD_9 = \alpha L e^{\beta/\lambda_9} + s + 1.49w + C \quad \text{Eq. 12}$$

In Equations 3–12, $\alpha$ and $\beta$ are constants, L is the path length, w is the water absorption in the water channel (here, channel 6), s is the wavelength independent scattering effect, and $\lambda_n$ is the wavelength of the nth channel. p and q are constants that represent the tiny absorptions from oil in channels 5 and 6, respectively. A, B, and C represent the molecular vibration absorptions from methane and oil in channels 0, 8, and 9. Using Equation 10 as an example, the first term ($\alpha L e^{\beta/\lambda_0}$) represents color absorptions, the second term (s) represents scattering, the third term (0.172 w) represents water absorptions, and the fourth term (A) represents the molecular vibration absorptions from methane and oil. Methods for determining contamination and GOR from constants, such as A, B, and C, are well known in the art. For example, U.S. Pat. No. 6,476,384 to Mullins, et al. discloses methods for determining GOR.

The ten individual equations defined in Equations 3–12 include seven unknown variables. Thus, valid OD measurements from only seven channels are required to solve the system of equations for the unknowns, including A, B, and C. If data from more channels are available, the most reliable seven may be selected to solve the system of equations, or a minimization algorithm may be used to solve the system of equations with all available channels. Minimization algorithms are well known in the art.

It is noted that the invention is not limited to the specific equations shown in Equations 3–12. These specific equations are used only as an example. Those having ordinary skill in the art will realize that other forms of these equations could be used without departing from the scope of the invention. For example, the coefficients of the water absorption in the water channel (w in channel 6) are typically determined by experiment. Thus, a different experiment may yield different results. Further, a different optical sensor may use channels with different wavelengths of light. The coefficients for each channel may be different than those shown in this example.

In some embodiments, the system of equations include a wavelength dependent scattering component. Instead of using a constant, s, for the scattering component in every channel, a wavelength dependent scattering component is used in place of the constant. In some embodiments, the wavelength dependent scattering component has the form $s + d/\lambda_n$, where s is the wavelength independent scattering effect, d is scattering constant, and $\lambda_n$ is the wavelength of the $n^{th}$ channel.

$$OD_1 = \alpha L e^{\beta/\lambda_1} + s + d/\lambda_1 - 0.020w \quad \text{Eq. 13}$$

$$OD_2 = \alpha L e^{\beta/\lambda_2} + s + d/\lambda_2 - 0.021w \quad \text{Eq. 14}$$

$$OD_3 = \alpha L e^{\beta/\lambda_3} + s + d/\lambda_3 - 0.020w \quad \text{Eq. 15}$$

$$OD_4 = \alpha L e^{\beta/\lambda_4} + s + d/\lambda_4 - 0.015w \quad \text{Eq. 16}$$

$$OD_5 = \alpha L e^{\beta/\lambda_5} + s + d/\lambda_5 + 0.022w + p \quad \text{Eq. 17}$$

$$OD_6 = \alpha L e^{\beta/\lambda_6} + s + d/\lambda_6 + w + q \quad \text{Eq. 18}$$

$$OD_7 = \alpha L e^{\beta/\lambda_7} + s + d/\lambda_7 + 0.228w \quad \text{Eq. 19}$$

$$OD_0 = \alpha L e^{\beta/\lambda_0} + s + d/\lambda_0 + 0.172w + A \quad \text{Eq. 20}$$

$$OD_8 = \alpha L e^{\beta/\lambda_8} + s + d/\lambda_8 + 0.187w + B \quad \text{Eq. 21}$$

$$OD_9 = \alpha L e^{\beta/\lambda_9} + s + d/\lambda_9 + 1.49w + C \quad \text{Eq. 22}$$

The system of equations in Equations 13–22 has ten equations and eight unknowns. Thus, valid OD data is needed for only eight of the channels to be able to solve Equations 13–22 for A, B, and C.

Figure 13:
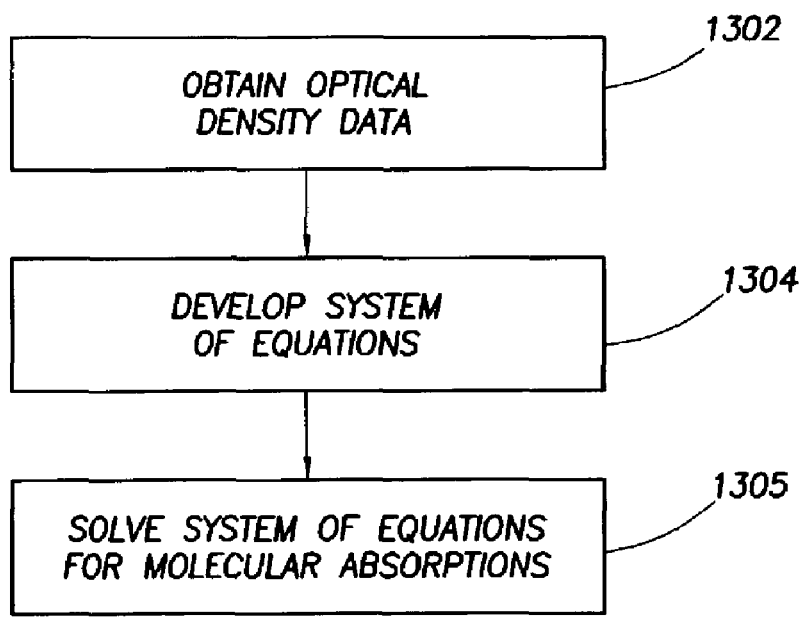
FIG. 13 shows one embodiment of a method according to the invention.

FIG. 13 shows a method according to one embodiment of the present invention. The method first includes obtaining data related to the OD of a fluid sample in a plurality of optical channels (shown at step 1302). In some embodiments, the data is collected at a plurality of times during the sampling process. The data may comprise the OD in the desired channels, or it may comprise another type of data that is related to the OD, for example the transmittance. Also, in some embodiments, the data is obtained by measurement, while in some other embodiments, the data comprises previously measured data, and it is obtained from storage media.

The method next includes developing a system of equations that model the OD of the fluid sample in each of the optical channels as the sum of color absorptions, molecular vibration absorptions, water absorptions, and scattering (shown at step 1304). In some embodiments the sum includes only two of the above factors, and in at least one embodiment the sum includes three of the above factors. In some embodiments, the color absorptions are determined by a function of wavelength. In at least one embodiment, the system of equations corresponds to Equations 3–12.

In some embodiments, the scattering is a function of wavelength. In at least one embodiment, the system of equations corresponds to Equations 13–22.

The method next includes solving the system of equations for the molecular vibrations in the methane channel and the oil channel (shown at step 1305). In some embodiments, the equations are solved at each of the plurality of times.

In some embodiments, the invention relates to an electronics system that is capable of receiving OD data and performing embodiments of the methods described above.

In one embodiment, the electronics system includes a memory, an input device adapted to receive OD data, and a processor. The processor may be adapted to use the data to develop a system of equations that model the optical density in each of the plurality of optical channels as a sum of at least two of the group consisting of a wavelength dependent function of color absorptions, molecular vibration absorptions, water absorptions, and scattering, and solve the system of equations to determine the molecular vibration absorptions in a methane channel and an oil channel.

An electronics system according to some embodiments of the invention is adapted to be operatively coupled to a downhole sampling tool. In other embodiments, an electronics system may be adapted to be integral with a downhole sampling tool.

Embodiments of the present invention may include one or more of the following advantages. In some embodiments, the invention enables refinement of OD signals from a downhole fluid analyzer when the signals are affected by the color of the fluid sample. Advantageously, in certain embodiments the invention enables the refinement of OD signals in circumstances where the signal is affected by water in the fluid sample. Advantageously, in certain embodiments the invention enables the refinement of OD signals in circumstances where the signal is affected by scattering of the incident light in the fluid sample. Signal refinement enables a more accurate determination of contamination, GOR, or any other important fluid property that may be determined by fluid analysis.

Advantageously, in certain embodiments the invention enables the refinement of OD signals in circumstances where the signal is affected by more than one of color, water, and scattering in the fluid sample. In some embodiments, the invention enables signal refinement of OD signals in the circumstance where the signal is affected by color, water, and scattering. In at least one embodiment, the invention enables the simultaneous removal of color effects, water effects, and scattering effects, providing for a more accurate determination of contamination, GOR, or other fluid properties.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for refining fluid sample data, comprising:
    obtaining optical density data for a fluid sample in at least one color channel and at least one fluid component channel;
    determining a color-absorption function from the optical density data for the fluid sample in the at least one color channel;
    calculating a portion of an optical density in the at least one fluid component channel caused by color absorptions; and
    de-coloring the optical density data for the at least one fluid component channel by removing the portion of the optical density in the at least one fluid component channel caused by color absorption.

2. The method of claim 1, wherein the at least one color channel comprises at least two color channels and the color-absorption function comprises two unknowns.

3. The method of claim 1, wherein the determining the color-absorption function, the calculating the portion of the optical density caused by color absorptions, and the de-coloring are performed on optical density data collected at a plurality of times.

4. The method of claim 1, wherein the color-absorption function is dependent on a wavelength of an incident light.

5. The method of claim 1, wherein the at least one fluid component channel comprises one selected from the group consisting of a methane channel, an oil channel, and both the methane channel and the oil channel.

6. The method of claim 1, further comprising calculating a gas-oil ratio of the fluid sample.

7. The method of claim 1, further comprising calculating a percent contamination of the fluid sample.

8. The method of claim 1, further comprising:
    obtaining optical density data for the fluid sample in a base channel;
    calculating a portion of an optical density in the base channel caused by color absorptions from the color-absorption function;
    de-coloring the optical density data in the base channel by removing the portion of the optical density in the base channel caused by color absorption; and
    de-scattering the optical density data for the at least one fluid component channel by removing the optical density of the base channel from the optical density of the at least one fluid component channel.

9. A method for refining fluid sample data, comprising:
    obtaining optical density data for a fluid sample in a water channel and in at least one fluid component channel;
    calculating a portion of an optical density in the at least one fluid component channel caused by water absorptions based on an optical density in the water channel and a water-absorption ratio for the at least one fluid component channel; and
    de-watering the optical density data in the at least one fluid component channel by removing the portion of the optical density in the at least one fluid component channel caused by water absorptions.

10. The method of claim 9, wherein the calculating the portion of the optical density data caused by water absorptions and the de-watering are performed on optical density data collected at a plurality of times.

11. The method of claim 9, wherein the water-absorption ratio is determined by experimentation.

12. The method of claim 9, wherein the at least one fluid component channel comprises one selected from the group consisting of a methane channel, an oil channel, and both the methane channel and the oil channel.

13. The method of claim 9, further comprising:
    obtaining optical density data for the fluid sample in a base channel; and
    calculating a portion of an optical density in the base channel caused by water absorptions based on the optical density in the water channel and a water-absorption ratio for the base channel;
    de-watering the optical density data in the base channel by removing the portion of the optical density caused by water absorptions in the base channel; and
    de-scattering the optical density data for the at least one fluid component channel by removing the optical density of the base channel from the optical density of the at least one fluid component channel.

14. The method of claim 9, further comprising calculating a gas-oil ratio of the fluid sample.

15. The method of claim 9, further comprising calculating a percent contamination of the fluid sample.

16. A method for refining fluid sample data, comprising:
obtaining optical density data for a fluid sample in at least one color channel, a water channel, and at least one fluid component channel;
determining a color-absorption function from the optical density data of the fluid sample in the at least one color channel;
calculating a portion of an optical density in the at least one fluid component channel caused by color absorptions;
calculating a portion of the optical density in the at least one fluid component channel caused by water absorptions based on an optical density in the water channel and a water-absorption ratio for the at least one fluid component channel; and
adjusting the optical density data in the at least one fluid component channel by removing the portion of the optical density in the at least one fluid component channel caused by color absorptions, and by removing the portion of the optical density in the at least one fluid component channel caused by water absorptions.

17. The method of claim 16, wherein the at least one color channel comprises two color channels and the color-absorption function comprises two unknowns.

18. The method of claim 16, wherein the determining the color-absorption function, the calculating a portion of the optical density in the at least one fluid component channel caused by color absorptions, the calculating a portion of the optical density in the at least one fluid component channel caused by water absorptions, and the adjusting the optical density data are performed on optical density data collected at a plurality of times.

19. The method of claim 16, further comprising:
obtaining optical density data for a fluid sample in a base channel;
calculating a portion of an optical density in the base channel caused by color absorptions from the color-absorption function;
calculating a portion of the optical density in the base channel caused by water absorptions based on the optical density in the water channel and a water-absorption ratio for the base channel;
adjusting the optical density data in the base channel by removing the portion of the optical density in the base channel caused by color absorptions, and by removing the portion of the optical density in the base channel caused by water absorptions; and
de-scattering the optical density data for the at least one fluid component channel by removing the optical density in the base channel from the optical density in the at least one fluid component channel.

20. A method for refining fluid sample data, comprising:
obtaining optical density data for a fluid sample in a plurality of optical channels;
developing a system of equations that model an optical density in each of the plurality of optical channels as a sum of at least two of the group consisting of color absorptions, molecular vibration absorptions, water absorptions, and scattering; and
solving the system of equations to determine the molecular vibration absorptions in at least a methane channel and an oil channel.

21. The method of claim 20, wherein the developing the system of equations and the solving the system of equations are performed on optical density data collected at a plurality of times.

22. The method of claim 20, wherein the at least two of the group consisting of color absorptions, molecular vibration absorptions, water absorptions, and scattering comprises a wavelength function of color absorptions.

23. The method of claim 20, wherein the at least two of the group consisting of color absorptions, molecular vibration absorptions, water absorptions, and scattering comprises a wavelength function of water absorptions.

24. The method of claim 20, wherein the at least two of the group consisting of color absorptions, molecular vibration absorptions, water absorptions, and scattering comprises a wavelength function of scattering.

* * * * *